(12) United States Patent
Albrecht et al.

(10) Patent No.: US 8,153,111 B2
(45) Date of Patent: Apr. 10, 2012

(54) PHOTO-TRIGGERED RELEASE OF ACTIVE SUBSTANCES FROM DENDRIMER-PHOTOSENSITIZER COMPLEXES

(75) Inventors: Volker Albrecht, Jena (DE); Arno Wiehe, Berlin (DE); Beate Roeder, Falkansee (DE); Wolfgang Neuberger, F.T. Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 1483 days.

(21) Appl. No.: 10/871,676

(22) Filed: Jun. 18, 2004

(65) Prior Publication Data

US 2005/0281777 A1    Dec. 22, 2005

(51) Int. Cl.
*A61K 31/00* (2006.01)
*A61K 9/00* (2006.01)

(52) U.S. Cl. .............. 424/78.3; 424/400; 424/DIG. 16; 525/420.5

(58) Field of Classification Search ................. 424/78.3, 424/484, 450, DIG. 16; 525/420.5
See application file for complete search history.

(56) References Cited

U.S. PATENT DOCUMENTS

| | | | |
|---|---|---|---|
| 5,795,581 A | 8/1998 | Segalman et al. | |
| 5,919,442 A | 7/1999 | Yin et al. | |
| 6,333,051 B1 * | 12/2001 | Kabanov et al. | 424/484 |
| 6,416,785 B1 * | 7/2002 | Riesenberg et al. | 424/450 |
| 7,582,744 B2 * | 9/2009 | Manoharan et al. | 536/24.5 |
| 2003/0176325 A1 * | 9/2003 | Nielsen et al. | 514/8 |
| 2005/0256069 A1 * | 11/2005 | Manoharan et al. | 514/44 |
| 2009/0286973 A1 * | 11/2009 | Manoharan et al. | 540/5 |

FOREIGN PATENT DOCUMENTS
WO    WO 01/08704 A2 *    2/2001

OTHER PUBLICATIONS

Bosman et al, "About Dendrimers: Structure, Physical Properties, and Applications", Chem. Rev. 1999, p. 1665-1688, v. 99, American Chem. Society.
Patri et al, "Dendritic polymer macromolecular carriers for drug delivery", Current Opinion in Chemical Biology 2002, p. 466-471, v. 6, Elsevier Science Ltd.
Gorman et al, "Structure-Property Relationships in Dendritic Encapsulation", Acc. Chem. Res. 2001, p. 60-71, v. 34, American Chem. Society.

(Continued)

*Primary Examiner* — Blessing Fubara
(74) *Attorney, Agent, or Firm* — B J Associates; Bolesh J. Skutnik

(57) ABSTRACT

Compositions of dendrimer-photosensitizer complexes including therapeutic molecules, and methods for their synthesis and use are disclosed. The therapeutic molecules and the photosensitizers are each covalently attached to the dendrimer at its end-groups, essentially randomly. Upon exposure to radiation of a suitable wavelength, the photosensitizers are activated to break up the dendrimer structure and thus release the therapeutic molecules. In a preferred embodiment, the end-groups of the dendrimer are replaced with or covalently connected to therapeutic molecules and photosensitizers. In a further preferred embodiment, targeting molecules may also be attached to the dendrimer to create a more accurate treatment. The present invention is especially useful for medical applications, where therapeutic molecules can be delivered to body areas for treatment of a variety of diseases without risk of premature release in the body, due to the strength and stability of the bonds between the end-groups and the photosensitizers and therapeutic molecules.

24 Claims, 5 Drawing Sheets

OTHER PUBLICATIONS

Smet et al, "Photolabile Dendrimers Using o-Nitrobenzyl Ether Linkages", Organic Letters 2000, p. 511-513, v. 2, American Chem. Society.

Bannwarth et al, "Clinical Pharmacokinetics of Low-Dose Pulse Methotrexate in Rheumatoid Arthritis", Clin. Pharmacokinet. Mar. 30, 1996, p. 194-210, v. 3, Adis Int'l Ltd.

Quintana et al, "Design & Function of a Dendrimer-Based Therapeutic Nanodevice Targeted to Tumor Cells Through the Folate Receptor", Pharm. Res. Sep. 2002, p. 1310-1316, v.19.

Kono et al, "Design of Dendritic Macromolecules Containing Folate or Methotrexate Residues", Bioconjugate Chem. 1999, p. 1115-1121, v. 10, American Chem Society.

Boffa et al, "Methotrexate for Psoriasis", Clinical and Experimental Dermatology 1996, p. 399-408, v. 21, Blackwell Science Ltd.

Hackbarth et al, "Photophysical Properties of pheophorbide-a-substituted diaminobutane poly-propylene-imine dendrimer", Chem. Phys. 2001, p. 339-346, v. 269, Elsevier Sci. BV.

Paul et al, "Comparative Study of the Photosensitization of Jurkat Cells in vitro by Pheophorbide-a and . . . ", Laser Physics 2003, p. 22-29, v. 13, Astro, Ltd.

Grayson et al, "Convergent Dendrons and Dendrimers: From Synthesis to Applications", Chem. Rev. 2001, p. 3819-3867, v. 101, American Chem. Society.

Fischer et al, "Dendrimers: From Design to Application—A Progress Report", Angew. Chem. Int. Ed. 1999, p. 884-905, v. 38, Wiley-VCH Verlag GmbH.

Ross et al, "The HER-2/neu Gene and Protein in Breast Cancer 2003: Biomarker and Target of Therapy", The Oncologist 2003, p. 307-325, v. 8, AlphaMed Press.

Patel et al, "A small, synthetic peptide for gene delivery via the serpin-enzyme complex receptor", J. Gene. Med. 2001, p. 271-279, v. 3, John Wiley & Sons, Ltd.

Eriksson et al, "Cell Permeabilization and Uptake of Antisense Peptide-Peptide Nucleic Acid (PNA) into *Escherichia coli*", J. of Biol. Chem. Mar. 1, 2002, p. 7144-7147, v. 277.

Sudimack et al, "Targeted drug delivery via the folate receptor", Advanced Drug Delivery Reviews 2000, p. 147-162, v. 41, Elsevier Science BV.

\* cited by examiner (PRIOR ART)

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Phe Asn Lys Pro Phe Val Phe Leu Ile
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 2

Cys Ser Ile Pro Pro Glu Val Lys Phe Asn Lys Pro Phe Val Phe Leu
1               5                   10                  15

Ile
```

```
<210> SEQ ID NO 3
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 3

Lys Phe Phe Lys Phe Phe Lys Phe Phe Lys
1               5                   10
```

PHOTO-TRIGGERED RELEASE OF ACTIVE SUBSTANCES FROM DENDRIMER-PHOTOSENSITIZER COMPLEXES

SUBMISSION ON COMPACT DISC

This application incorporates by reference the ASCII text file identified by the File Name 97353.00146_st25.txt, containing 2.0 KB of data, created on Nov. 11, 2009 and filed in computer-readable format (CRF).

BACKGROUND OF INVENTION

1. Field of the Invention

The present invention relates to the field of delivering therapeutic substances through the use of dendrimer-photosensitizer complexes.

2. Current State of the Art

Dendrimers are well known for their ability to connect with and aid delivery of pharmaceutically active substances. (examples: A. W. Bosman, H. M. Janssen, E. W. Meijer, About Dendrimers: Structure, Physical Properties, and Applications, *Chem. Rev.* 1999, 99, 1665-1688; A. K. Patri, I. J. Majoros, J. R. Baker Jr., Dendritic polymer macromolecular carriers for drug delivery, *Curr. Opin. Chem. Biol.* 2002, 6, 466-471; C. B. Gorman, J. C. Smith, Structure-Property Relationships in Dendritic Encapsulation, *Acc. Chem. Res.* 2001, 34, 60-71)

In principle, there are two ways to make such connections. In the first method, drug molecules are enclosed in the dendrimer by steric hindrance and/or non-covalent binding interactions. In another option, the drug molecules are covalently attached to the dendrimer. Only this latter method allows the transport of large numbers of drug molecules per dendrimer.

The problem of being unable to release the drug molecules at a certain site of the body arises particularly in the case of covalently coupled drug molecules. There currently exists no satisfactory solution for this problem. The existing concepts mainly rely on a slow metabolization of the dendrimer-drug complex.

Photolabile dendrimers (dendrimers that are destroyed if subjected to light, but without the participation of photosensitizers) are known, (M. Smet, L.-X. Liao, W. Dehaen, D. V. McGrath, Photolabile Dendrimers Using o-Nitrobenzyl Ether Linkages, *Org. Lett.* 2000, 2, 511-513) yet not in connection with the release of specific drugs. For application in the field of rheumatoid arthritis, (B. Bannwarth, F. Pehourcq, T. Schaeverbeke, J. Dehais, Clinical pharmacokinetics of low-dose pulse methotrexate in rheumatoid arthritis, *Clinic. Pharmacokin.* 1996, 30, 194-210), the synthesis of dendrimers with methotrexate residues at the dendrimer periphery has been described, but this approach lacks the element of photosensitizer-mediated drug release (as is described in the present invention). (A. Quintana, Antonio, E. Raczka, L. Piehler, I. Lee, A. Myc, I. Majoros, A. K. Patri, T. Thomas, J. Mule, J. R. Baker Jr., Design and Function of a Dendrimer-Based Therapeutic Nanodevice Targeted to Tumor Cells Through the Folate Receptor, *Pharmaceut. Res.* 2002, 19, 1310-1316; K. Kono, M. Liu, J. M. J. Frechet, Design of Dendritic Macromolecules Containing Folate or Methotrexate Residues, *Bioconj. Chem.* 1999, 10, 1115-1121) Methotrexate is also used for the treatment of psoriasis. (M. J. Boffa, R. J. Chalmers, Methotrexate for psoriasis, *Clinic. Experim. Dermatol.* 1996, 21, 399-408)

U.S. Pat. No. 5,919,442 by Rui et al describes the construction of "hyper comb-branched polymer conjugates," constructed from a generally linear chain core and successive generations of oligomers branching out, that allow the creation of multi-functional species for delivery of a variety of substances including bioactive agents, and chromophores (for signal amplification). It is not described that chromophores can be activated in any way to affect the carrier, and especially does not describe the chromophores as activatable by radiation to open or cleave the carrier molecule. Additionally, it is provided that the claimed hyper comb-branched polymer macromolecules may be constructed from dendrimer molecules as hyper-branched cores to which oligomer branches are attached. Embodiments are also provided that include a targeting agent attached to the conjugate. Conjugates consisting of hyper comb-branched polymers as carriers, and various materials are also described, wherein a variety of materials are attached to the conjugate in numerous ways, including being generally disposed within the branches, between layers or on the polymer surface, and linking the material through covalent bonding and a number of other bonding means. For release of material, chemical bonds may be cleaved. Although this patent provides macromolecules as carrier molecules for covalently attached therapeutic molecules, it does not provide photosensitizer-dendrimer complexes for predictable delivery and release of therapeutic substances, which is the new concept of the present invention. Also, there is provided no means for cleaving the polymers with radiation. Methods of release of molecules according to U.S. Pat. No. 5,919,442 include cleavage of chemical bonds such as by hydrolysis.

U.S. Pat. No. 5,795,581 describes a method for the controlled release of components from within the matrices of dendrimer/bioactive complexes. Release of the components can be achieved in numerous ways, such as by fragmenting the structure of the dendrimer. Another method involves fragmenting the complex where the fragments themselves become the therapeutic molecules.

In one embodiment, a "guest molecule" is trapped within a host molecule. There is no covalent bonding: the guest molecule is trapped within pockets of the host molecule, which is preferably a dendrimer. Upon exposure to radiation such as bright sunlight, the structure of the host molecule is altered to allow escape of the guest molecule. The alteration can be accomplished in three ways. First, a volatile component such as water can be driven from the host molecule. Second, sunlight can interact with some of the bonds, causing the host structure to expand. Third, the sunlight can cause host bonds to rupture. Inclusion (by means other than covalent bonding) of a chromophore into the core dendrimer molecule is mentioned as a means to facilitate reactions of the core molecule or branches. For medical applications such as cancer, the host molecules can be introduced and radiation applied to cancerous areas to increase the specificity of the treatment. U.S. Pat. No. 5,795,581 describes the physical entrapment of active molecules in the dendrimer structure which may then be released by an external stimulus including electromagnetic radiation.

Other uses for dendrimers include acting as carrier molecules for photosensitizers in photodynamic therapy, as described in W.O. Patent No. 01/08704, which is fully included here as a reference and shares inventorship and ownership with the present invention, and in related literature. (see S. Hackbarth, V. Horneffer, A. Wiehe, F. Hillenkamp, B. Röder, *Chem. Phys.* 2001, 269, 339-346) The above references describe the synthesis of a dendrimer having its periphery substituted with photosensitizers (pheophorbide a, see FIG. 1). When dendrimers 101 are exposed to light, fragmentation of the dendrimer occurs which generates fragments that predominantly contain 1 or 2 pheophorbide a molecules 103 (the molecules represented by pheophorbide a may be replaced by hydrogen at desired points). Pheophorbide a are photodynamically active species that can generate singlet oxygen. (A. Paul, S. Hackbarth, A. Moelich, C. Luban, S. Oelckers, F. Boehm, B. Roeder, Comparative study of the photosensitization of Jurkat cells in vitro by pheophorbide-a and a pheophorbide-a diaminobutane poly-propylene-imine dendrimer complex, *Laser Phys.* 2003, 13, 22-29) The fragmentation of the dendrimer upon exposure to light is due to the reaction of singlet oxygen with the dendrimer backbone because control experiments revealed that the dendrimer is only photolabile in the presence of the photosensitizer and molecular oxygen.

Those results show that it is in principle possible to build photolabile dendrimers by substituting end-groups with photosensitizers. Such dendrimers can be used to deliver the photosensitizers (or relevant fragments containing the photosensitizers) upon exposure to light. The art is aimed solely at the release of photosensitizers; there is no teaching to suggest that photosensitizers could be used as a means to release other species.

Thus there exists no quick and controllable way to release therapeutic molecules from dendrimers to which they are covalently attached. The present invention addresses this need.

OBJECTIVES AND BRIEF SUMMARY OF THE INVENTION

It is an object of the present invention to provide a method and composition for controllably delivering molecules to a desired location.

It is another object of the present invention to provide a method and composition for controllably releasing therapeutic molecules to a body area.

It is yet another object of the present invention to provide a method and composition for carrying and releasing therapeutic molecules with greater control than previous methods and compositions.

Briefly stated, the present invention provides compositions of dendrimer-photosensitizer complexes including therapeutic molecules, and methods for their synthesis and use. The therapeutic molecules and the photosensitizers are each covalently attached to the dendrimer at its end-groups, essentially randomly. Upon exposure to radiation of a suitable wavelength, the photosensitizers are activated to break up the dendrimer structure and thus release the therapeutic molecules. In a preferred embodiment, the end-groups of the dendrimer are replaced with or covalently connected to therapeutic molecules and photosensitizers. In a further preferred embodiment, targeting molecules may also be attached to the dendrimer to create a more accurate treatment. The present invention is especially useful for medical applications, where therapeutic molecules can be delivered to body areas for treatment of a variety of diseases without risk of premature release in the body, due to the strength and stability of the bonds between the end-groups and the photosensitizers and therapeutic molecules.

The above, and other objects, features and advantages of the present invention will become apparent from the following description read in conjunction with the accompanying drawings, (in which like reference numbers in different drawings designate the same elements.)

DETAILED DESCRIPTION OF PREFERRED EMBODIMENTS

The present invention provides novel methods and compositions for effectively and controllably delivering therapeutic molecules to body areas for treatment of a wide variety of illnesses and conditions.

The prior art teaches three main concepts: 1) active molecules can be incorporated into dendrimers and released using physical or chemical methods, 2) active molecules can be covalently bonded to the dendrimer periphery and released by enzymatic processes, and 3) photosensitizers can be covalently bonded to the dendrimer periphery and released by radiation.

The present invention provides the new concept of attaching individually both photosensitizers and active molecules together, essentially randomly, on the periphery of a dendrimer. The active molecule and photosensitizer are each bonded to separate branches of the dendrimer, for delivery and release of the active molecule. The photosensitizer acts as a mechanism to break the dendrimer branch or branches and release the active molecule. This invention allows for predictable release: there is no risk of accidental premature release due to the strength of the covalent bonding, and instantaneous release can be achieved (in contrast to the relatively slow enzymatic release required by the prior art). Also, release can be achieved with relatively harmless low intensity light.

The concept of the present invention exploits the ability of dendrimers to bind a large number of molecules at their end-groups (S. M. Grayson, J. M. J. Frechet, Convergent Dendrons and Dendrimers: from Synthesis to Applications, *Chem. Rev.* 2001, 101, 3819-3867; M. Fischer, F. Vögtle, Dendrimers: From Design to Application-A Progress Report, *Angew. Chem. Int. Ed.* 1999, 38, 885-905) and the ability of photosensitizers to generate singlet oxygen. The basis of the present invention is the synthesis of complexes containing dendrimers linked with photosensitizers for delivery of therapeutic substances (especially non-photosensitizers) to treatment areas. A preferred embodiment of the present invention is in the form of a molecule given in FIG. 2 (the depicted dendrimer structure is chosen arbitrarily).

Figure 1:
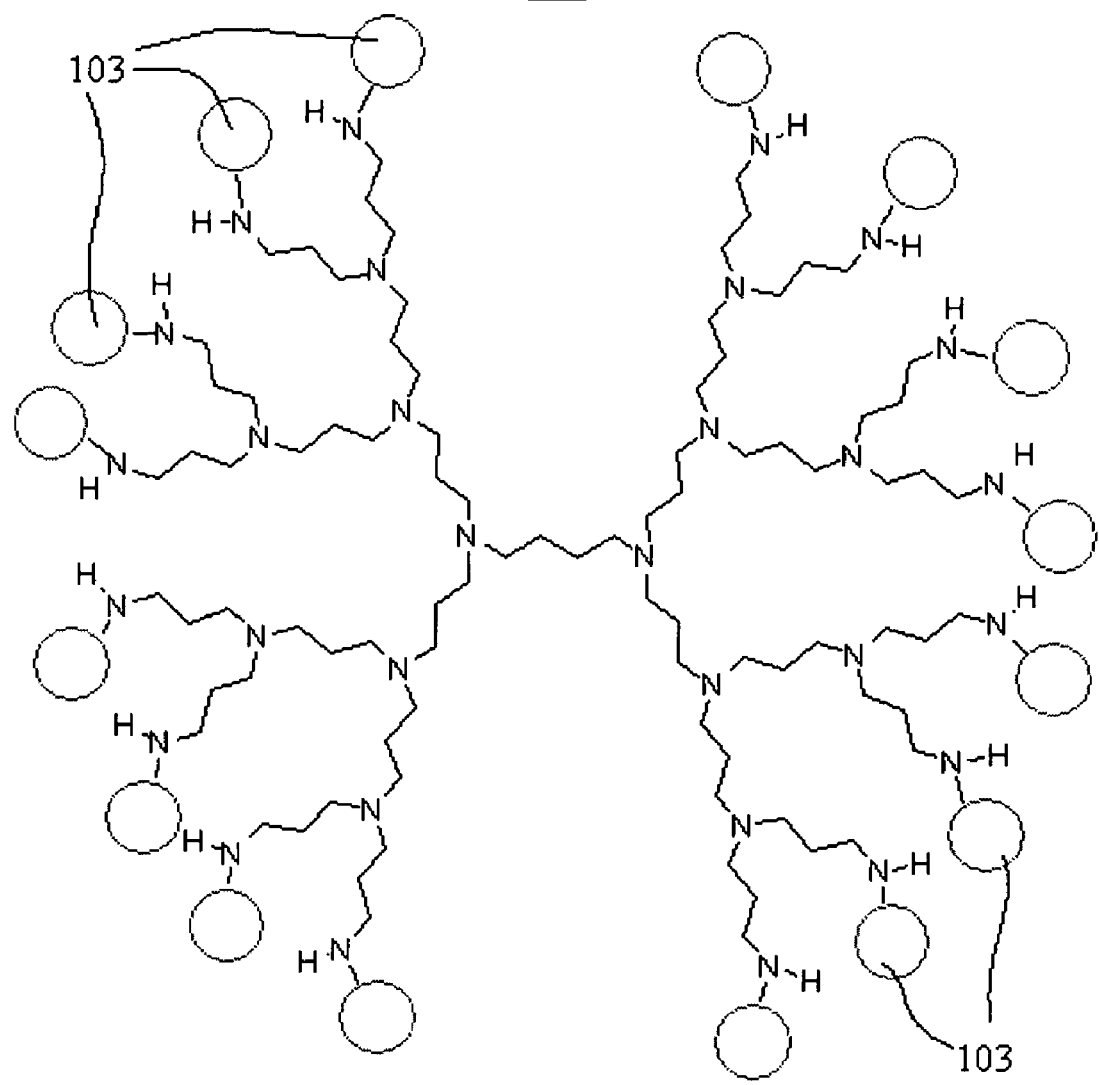
FIG. 1—Diagram of a prior art Pheophorbide a-dendrimer.
Figure 2:
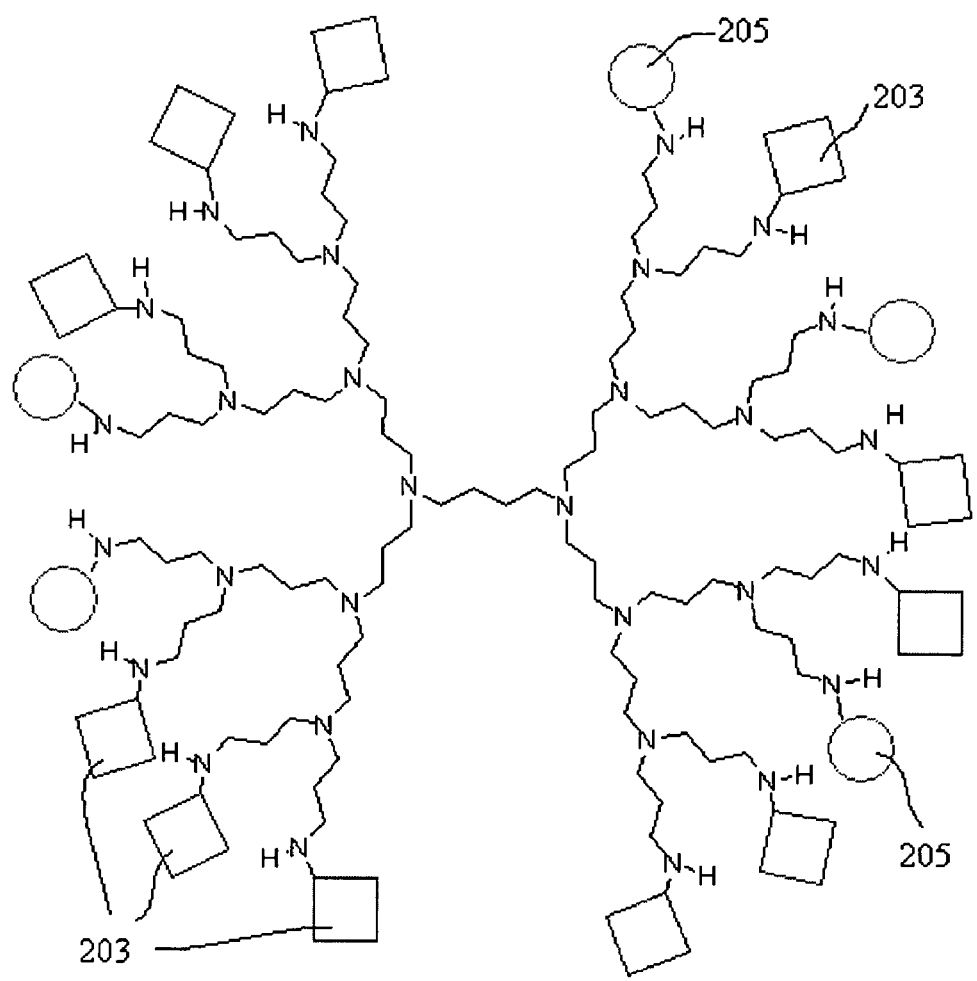
FIG. 2—Diagram of a dendrimer-drug complex with attached photosensitizers.

As shown in FIG. 2, the end-groups of dendrimer complex 201 are substituted with, or covalently connected to, drug molecules 203 and photosensitizers 205. These complexes serve as drug-depots in the body, from which drug molecules 203 are released when desired simply by applying light of a certain wavelength to the treatment area. When complex 201 is exposed to light of a particular wavelength, photosensitizers 205 generate singlet oxygen that destroys bonds within the dendrimer and releases the drug molecules or fragments containing the drug molecules (and may also contain one or more photosensitizer molecules). Activation of photosensitizers 205 serves to cleave the dendrimer structure at a desired time to release drug molecules 203.

Unlike the prior art, which has disclosed the transport and release of therapeutic molecules that are trapped within the dendrimer (steric hindrance), the present invention discloses dendrimer compounds wherein therapeutic molecules and photosensitizers are covalently bonded to dendrimer branches. This covalent attachment of both the active molecule and photosensitizer ensures that the therapeutic molecules remain securely bound to the dendrimer until they are finally released by specific light stimulus. This is advantageous over other types of bonding or interaction, specifically non-covalent bonds which are weaker or less stable. Such bonds would pose a significant risk of being released to soon, such as at any time after application.

Additionally, because release is accomplished by photodynamic action, in contrast to thermal reaction by radiation in the prior art, release can be precisely controlled. Activation of the photosensitizers of the present invention produces radicals such as singlet oxygen, which act to break the chains to which active molecules are bonded and release the active molecules. Because singlet oxygen has a very limited range of action, it can be activated so that only the dendrimer bonds are broken, and can avoid affecting other molecules or cells, which is a danger of methods that use thermal or chemical release. Also, because the photosensitizers are activated by specific wavelengths, release can be more easily controlled and the risk of inadvertent or premature release, such as by unintended irradiation by ambient light, can be eliminated.

Figure 3:
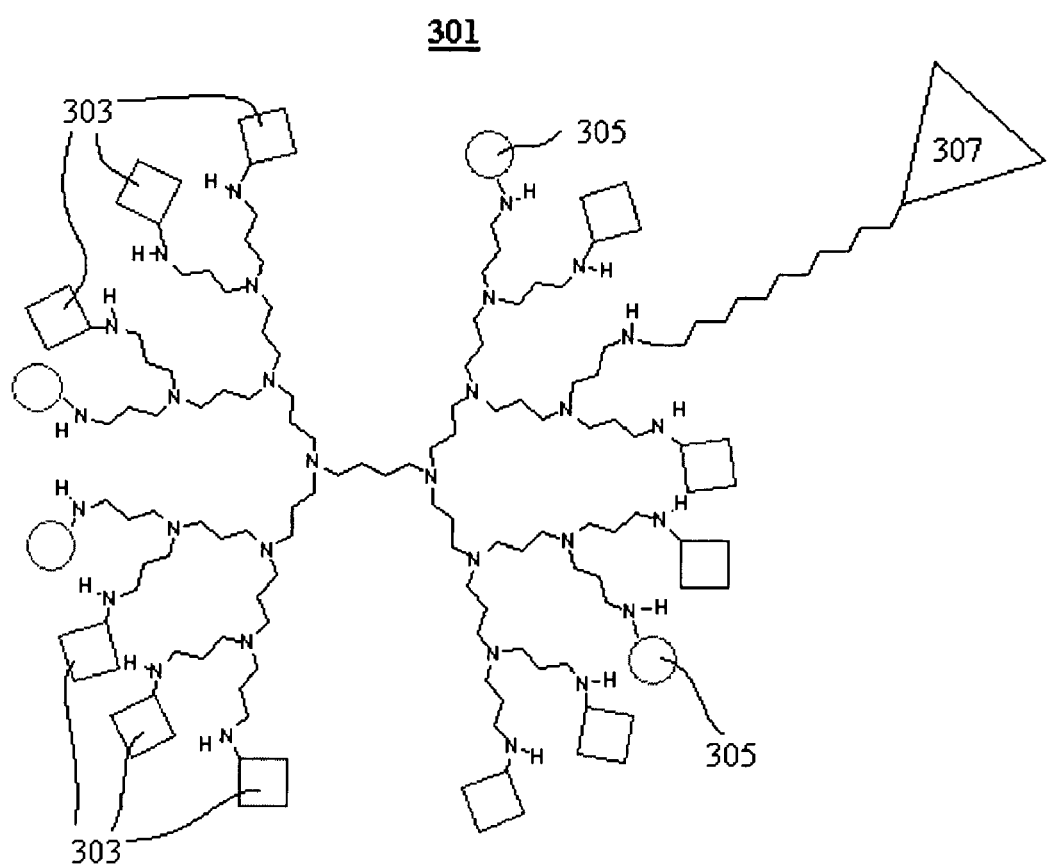
FIG. 3—Dendrimer-drug complex with attached photosensitizers and targeting molecule or moiety for site-specific targeting.

Complexes such as those depicted in FIG. 2 generally are not able to specifically target certain sites of the body for drug delivery. To ensure site-specific targeting a suitable addressing molecule, such as an antibody or antibody fragment, can be coupled to the complex. This is illustrated in FIG. 3. As shown there, dendrimer complex 301 contains drug molecules 303 and photosensitizer molecules 305 as substitutes for, or additions to, the normal dendrimer end-groups. Targeting molecule 307 is substituted for, or connected to, one of the end-groups of dendrimer 301 and serves to direct dendrimer complex 301 to the desired treatment area.

One example of a targeting molecule that can be utilized with the present invention is the site-specific monoclonal antibody Herceptin (also known as Trastuzumab). Herceptin targets cancer cells that overexpress a protein called HER-2 or erb B2, which is found on the surface of cancer cells. Herceptin slows or stops the growth of these cells. Approximately 25 to 30 percent of breast cancers overexpress HER-2. These tumors tend to grow faster and are generally more likely to recur than tumors that do not overproduce HER-2 (J. S. Ross, J. A. Fletcher, G. P. Linette et al., The Her-2 Gene and Protein in Breast Cancer 2003: Biomarker and Target of Therapy, *The Oncologist* 2003, 8, 307-325).

Another strategy includes the screening and development of tumor site-specific synthetic peptides. The serpin-enzyme complex receptor (SECR) has previously been successfully targeted for gene delivery using synthetic peptide ligands covalently linked in fluid phase to commercially available polylysine preparations. Two synthetic peptides designated polylysine antitrypsin 1 (PAT1) ($K_{16}$ FNKPFVFLI, SEQ ID NO:1) and polylysine antitrypsin 2 (PAT2)($K_{16}$ CSIPPEVK-FNKPFVFLI, SEQ ID NO:2) were evaluated for gene delivery (for further description of these peptides, see S. Patel, X. Zhang, L. Collins, J. W. Fabre, A small, synthetic peptide for gene delivery via the serpin-enzyme complex receptor, *J. Gene Med.* 2001,3, 271-279). In parallel, this strategy can be also applied for targeting bacteria. The peptide KFFKFFK-FFK (SEQ ID NO:3) improves cell permeabilization and uptake of antisense peptide-peptide nucleic acid (PNA) into *Escherichia coli* (for further description of this peptide, see M Eriksson, P. E. Nielsen, L. Good, Cell permeabilization and uptake of antisense peptide-peptide nucleic acid (PNA) into *Escherichia coli*, *J. Biol. Chem.* 2002, 277, 7144-7147).

Another example of a targeting molecule is Folic acid, employed for tumor targeting. Folic acid, a high affinity ligand of the folate receptor, retains its receptor binding properties when derivatized via its gamma-carboxyl. Folate conjugation, therefore, presents an alternative method of targeting the folate receptor. The folate receptor is a highly selective tumor marker overexpressed in greater than 90% of ovarian carcinomas. This strategy has been successfully applied in vitro for the receptor-specific delivery of protein toxins, anti-T-cell receptor antibodies, interleukin-2, chemotherapy agents, gamma-emitting radiopharmaceuticals, magnetic resonance imaging contrast agents, liposomal drug carriers, and gene transfer vectors (J. Sudimack, R. J. Lee, Targeted drug delivery via the folate receptor, *Adv. Drug Deliv. Rev.* 2000, 41, 147-162).

Dendrimers of many forms, sizes and types may be utilized in the complexes and methods of the present invention, and the form may vary depending on the type of therapeutic molecule delivered and/or the type of tissue treated. Exemplary dendrimers include starburst dendrimers and dendrimers constructed from linear or branched chains of dendrones.

In a preferred method of use of the complexes described above, a therapeutic dendrimer complex according to the present invention is synthesized (see examples below) by covalently bonding multiple photosensitizer molecules and therapeutic molecules to dendrimers. The resulting complexes contain both photosensitizers and therapeutic molecules attached to the periphery of the dendrimer. If desired, the synthesis can be controlled so that each dendrimer molecule has a defined ratio of photosensitizers to therapeutic molecules. The complex is then applied to the treatment area. Application may be systemic, such as by vascular injection, or local application, such as by topical application or local injection.

Radiation is then applied to the treatment area. The radiation source may be of any type capable of delivering suitable activating radiation to the treatment area, including natural sunlight, non-coherent radiation such as from a lamp, or coherent radiation such as by a laser source. The source and methods of delivery may vary depending on the type of photosensitizer used and the type and location of affected tissue. For areas on or near the surface, sunlight or a lamp may be sufficient, whereas for interior locations, optical fibers or optical fiber bundles incorporated into catheters or probes may prove most useful. The radiation applied must be at least substantially of a wavelength sufficient to activate the photosensitizer.

Upon irradiation, the photosensitizer molecules react to form singlet oxygen, which acts to break bonds in the dendrimers and release the drug molecules or end-groups containing the drug molecules. This method is not limited to single applications or single therapeutic molecule applications. The therapeutic complexes according to the present invention may have more than one type of therapeutic molecule attached to the dendrimer molecule. Furthermore, application of the dendrimer complex may be accomplished by more than one administration prior to irradiation, or numerous sequential treatments each consisting of administration of the complex followed by irradiation.

An advantage of the present invention lies in its ability to allow great control over the location of drug release. Local administration may be one method of controlling drug release. Controllably applying radiation allows drug release to be even more accurate, and helps to increase the effectiveness and efficiency of the drug application. Because radiation can be highly controlled, the therapeutic complex can be administered at higher concentrations and over larger areas than would be possible if controlled administration were the only limiting factor. Because administration is not so limited in the present invention, the ability to apply larger concentrations over larger areas helps to ensure that drugs are present with sufficient concentration and consistency throughout the treatment area.

One useful application of such dendrimer-drug-photosensitizers-complexes is for the treatment of rheumatoid arthritis by utilizing the complexes to deliver anti-arthritis drugs such as methotrexate (which can also be used to treat psoriasis), though there are many other medical applications where such drug complexes can be effectively used.

Other useful applications include delivery of oligonucleotides to cells, delivery of antibody or sugar moieties, carriers for antisense oligonucleotides, and delivery of anti-cancer drugs such as 5-fluorouracil and adriamycin.

Examples of therapeutic drugs that can be delivered according to the present invention include fluorescence markers, anti-arthritic agents, and anti-cancer agents. Additional therapeutic substances include the following. This list is purely exemplary and does not limit the drugs that can be successfully delivered to treatment areas according to the present invention.

Further examples of therapeutic agents include folate antagonists (methotrexate, edatrexate), purine and pyrimidine antagonists (6-mercaptopurine, 5-fluorouracil, fludarabine), nitrogen mustard derivatives (cyclophosphamide, chlorambucil, melphalan), platinum compounds (cisplatin, carboplatin), nitrosoureas (carmustine, lomustine, ranimustine), anticancer antibiotics (doxorubicin, daunorubicin, menogaril, bleomycin, mitomycin), antimitotics (vincristine, vinblastine, taxol, taxotere, rhizoxin), etoposide, temiposide, and hormonal agents used for anti-cancer therapy (tamoxifen, droloxifene, flutamide).

Many of the known photosensitizers may be advantageously used with the present invention. Examples of useful photosensitizers include chlorophyll and its derivatives, porphyrins, pheophorbide (including pheophorbide a) and its derivatives, bacteriopheophorbide, chlorins and bacteriochlorins, porphycenes, texaphyrines, sapphyrines, phthalocyanines, and naphthalocyanines, and photosensitizer precursors such as 5-aminolevulinic acid.

The present invention is further illustrated by the following examples, but is not limited thereby.

EXAMPLE 1

Figure 4:
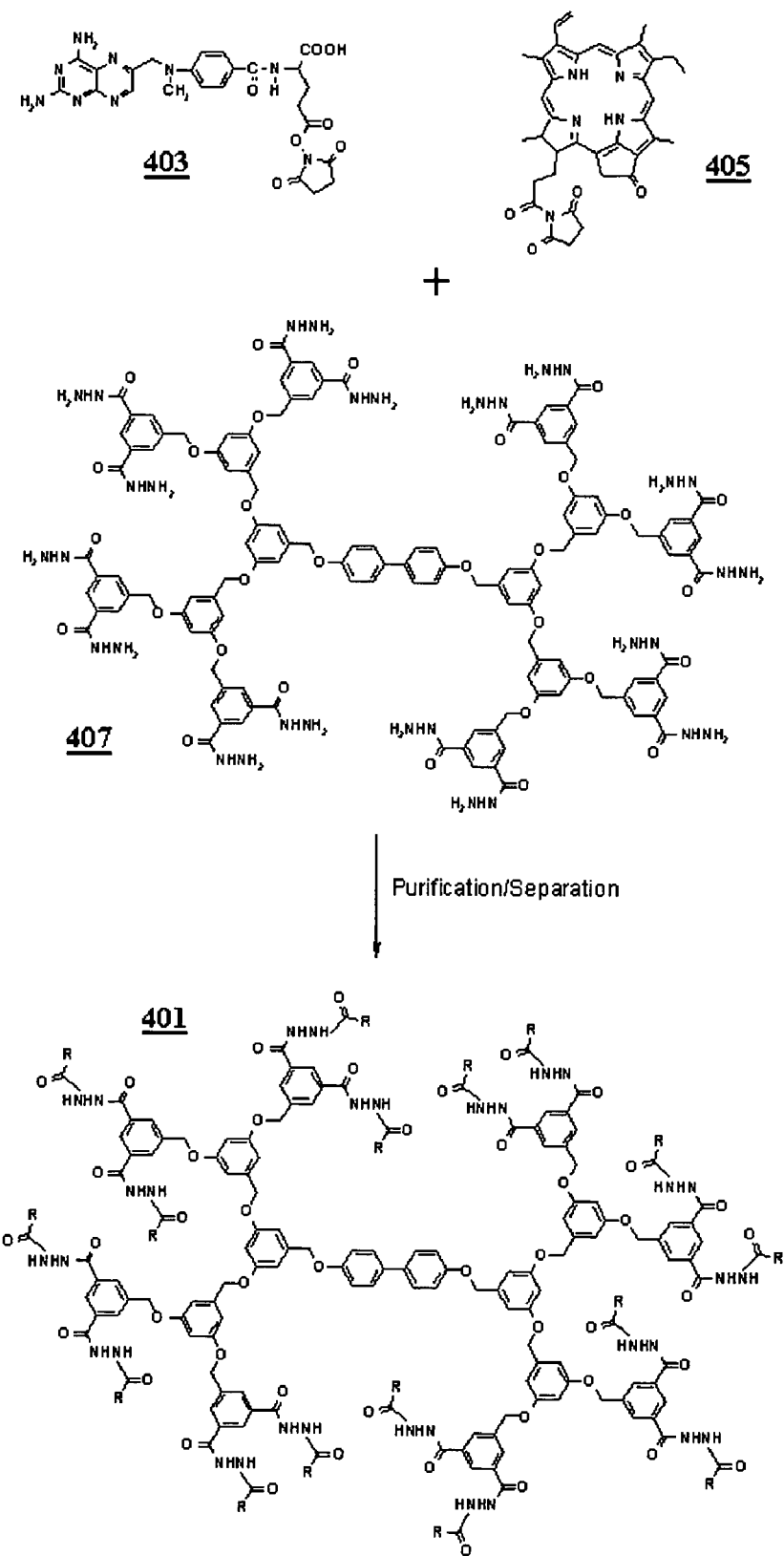
FIG. 4—Illustration of the synthesis of a methotrexate-pyropheophorbide-dendrimer complex.

The dendrimer-photosensitizer-therapeutic-molecule complexes are synthesized employing well-known methods of synthetic dendrimer chemistry. (see A. W. Bosman, H. M. Janssen, E. W. Meijer, About Dendrimers: Structure, Physical Properties, and Applications, Chem. Rev. 1999, 99, 1665-1688) A very simple method is the reaction of an active ester of the therapeutic molecule (e.g. methotrexate) and an active ester of a photosensitizer (e.g. pyropheophorbide a) with a dendrimer having suitable end-groups for coupling in a given molar ratio. Subsequent purification of the mixture yields dendrimers containing the desired amount of therapeutic molecules and photosensitizers. This is illustrated in FIG. 4, in which methotrexate molecules 403 and photosensitizer molecules 405 (in this example, in a molar ratio of 3:1, respectively) are reacted with dendrimer molecule 407 to yield dendrimer complex 401. In this example, photosensitizer 405 is pyropheophorbide, and thus complex 401 is a therapeutic methotrexate-pyropheophorbide complex, wherein R is a methotrexate or a pyropheophorbide molecule.

EXAMPLE 2

Figure 5:
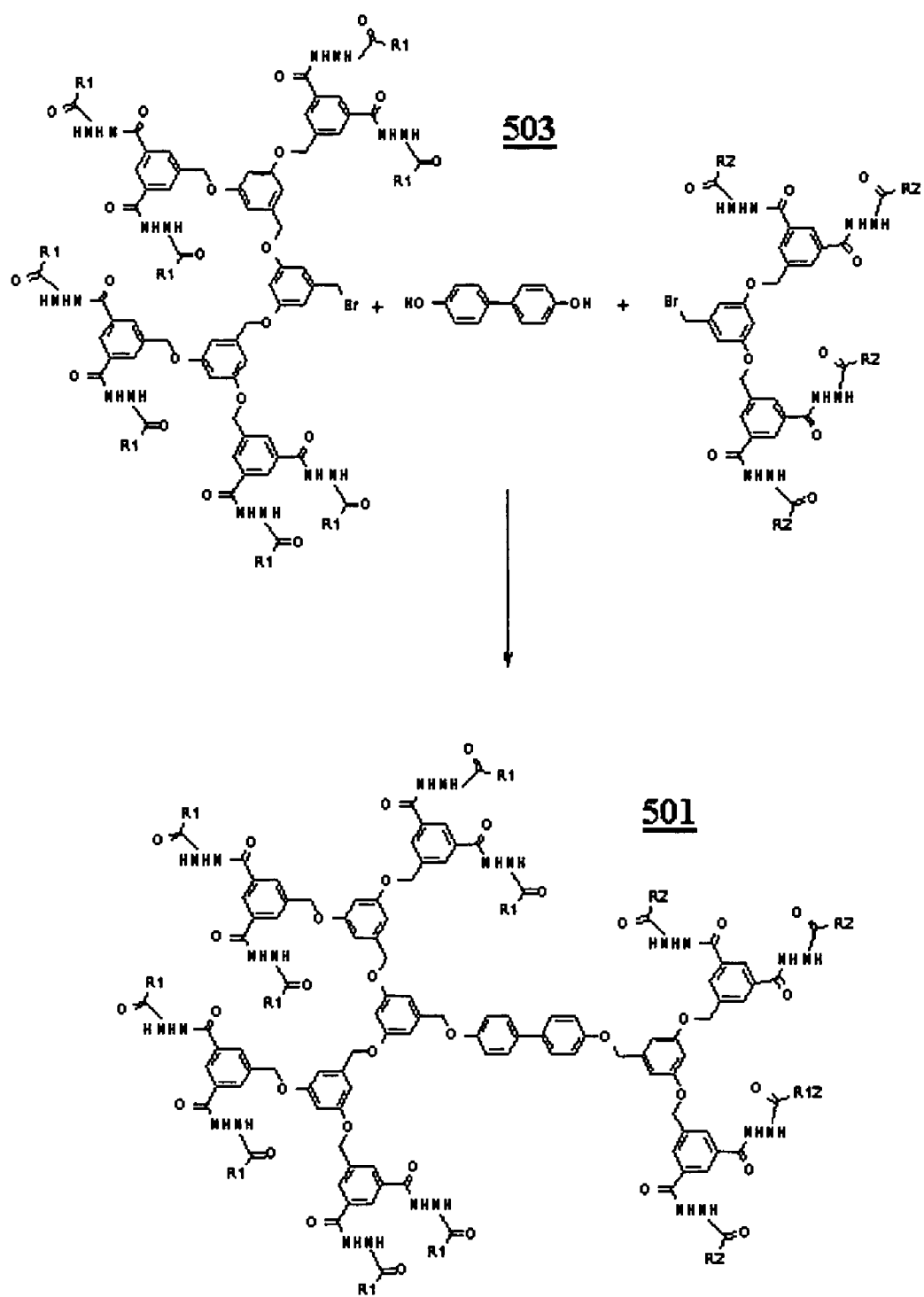
FIG. 5—Illustration of an alternate synthesis method for producing a therapeutic dendrimer complex.

As an alternative, the dendrimer-photosensitizer-therapeutic-molecule complexes are synthesized via a convergent synthetic strategy, as shown for example in FIG. 5, combining simple dendritic building blocks 503 to yield the final dendrimer 501.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

---

What is claimed is:

1. A therapeutic molecule delivery complex, comprising: a dendrimer molecule; multiple therapeutically active molecules selected from the group consisting of anti-cancer agents, folate antagonists, purine and pyrimidine antagonists, nitrogen mustard derivatives, platinum compounds and nitrosureas, and multiple photosensitizer molecules each individually connected by a covalent bond to an end-group of said dendrimer.

2. The therapeutic molecule delivery complex according to claim 1, wherein a number of therapeutic molecules and a number of said photosensitizer molecules attached to said dendrimer is in a preselected ratio.

3. The therapeutic molecule delivery complex according to claim 1, wherein said photosensitizers are selected from the group consisting of chlorophyll, pheophorbide, porphyrins, chlorins and bacteriochlorins, porphycenes, texaphyrines, sapphyrines, phthalocyanines, and naphthalocyanines.

4. The therapeutic molecule delivery complex according to claim 1, wherein said dendrimers are selected from the group consisting of starburst dendrimers and linear chains of dendrones and branched chains of dendrones.

5. The therapeutic molecule delivery complex according to claim 1, wherein more than one type of therapeutic molecule is connected to said dendrimer.

6. The therapeutic molecule delivery complex according to claim 1, further comprising at least one targeting molecule, wherein each said targeting molecule has an affinity to said treatment area and is covalently bonded to an end-group of said dendrimer.

7. The therapeutic molecule delivery complex according to claim 6, wherein said targeting molecules are peptides.

8. The therapeutic molecule delivery complex according to claim 7, wherein said targeting molecule is the peptide KFFKFFKFFK (SEQ ID NO:3).

9. The therapeutic molecule delivery complex according to claim 1, wherein said anti-cancer agent is antimitotic.

10. The therapeutic molecule delivery complex according to claim 9, wherein said antimitotics are selected from the group consisting of vincristine, vinblastine, taxol, taxotere, and rhizoxin.

11. The therapeutic molecule delivery complex according to claim 1, wherein said folate antagonists are selected from the group consisting of methotrexate and edatrexate.

12. The therapeutic molecule delivery complex according to claim 1, wherein said purine and pyrimidine antagonists are selected from the group consisting of 6-mercaptopurine, 5-fluorouracil, and fludarabine.

13. The therapeutic molecule delivery complex according to claim 1, wherein said nitrogen mustard derivatives are selected from the group consisting of cyclophosphamide, chlorambucil, and melphalan.

14. The therapeutic molecule delivery complex according to claim 1, wherein said platinum compounds are selected from the group consisting of cisplatin and carboplatin.

15. The therapeutic molecule delivery complex according to claim 1, wherein said nitrosoureas are selected from the group consisting of carmustine, lomustine, ranimustine.

16. The therapeutic molecule delivery complex according to claim 1, wherein said anticancer agents are antimitotics selected from the group consisting of doxorubicin, daunorubicin, menogaril, bleomycin, and mitomycin.

17. The therapeutic molecule delivery complex according to claim 1, wherein said anticancer agent are hormonal agents used for anti-cancer therapy, wherein said are hormonal agents used for anti-cancer therapy are selected from the group consisting of tamoxifen, droloxifene, and flutamide.

18. A method of medicinal therapy comprising the steps of:
applying therapeutic dendrimer complexes of claim 1 to a treatment area; and
irradiating said treatment area with radiation having a wavelength suitable to activate said photo sensitizers; and
releasing said therapeutically active molecules from said dendrimer.

19. The method according to claim 18, wherein said releasing is accomplished by activation of said photosensitizer to cause the destruction of a bond between said therapeutic molecule and an end-group of said dendrimer.

20. The method according to claim 18, wherein said releasing is accomplished by activation of said photosensitizer to cause the destruction of a bond between an end-group of said dendrimer containing said therapeutic molecule and an interior branch of said dendrimer to release a dendrimer fragment containing said therapeutic molecule.

21. The method according to claim 18, wherein said release is accomplished by activation of said photosensitizer to cause the destruction of a bond between an end-group and an interior branch of said dendrimer, thereby releasing a dendrimer fragment containing at least one said therapeutic molecule and at least one said photosensitizer.

22. The method according to claim 21, comprising the additional step of applying radiation of a suitable wavelength to activate said photosensitizer contained in said dendrimer fragment to cause destruction of a bond between said therapeutic molecule and said fragment, thereby releasing said therapeutic molecule from said fragment.

23. The method according to claim 18, where said radiation is selected from the group consisting of sunlight, noncoherent radiation, and laser radiation.

24. The method according to claim 18, wherein said complex is administered in more than one application.

* * * * *